US012109034B2

(12) United States Patent
Hara

(10) Patent No.: US 12,109,034 B2
(45) Date of Patent: Oct. 8, 2024

(54) REHABILITATION SUPPORT APPARATUS, METHOD THEREFOR, AND PROGRAM

(71) Applicant: mediVR, Inc., Osaka (JP)

(72) Inventor: Masahiko Hara, Osaka (JP)

(73) Assignee: MEDIVR, INC., Osaka (JP)

( * ) Notice: Subject to any disclaimer, the term of this patent is extended or adjusted under 35 U.S.C. 154(b) by 425 days.

(21) Appl. No.: 17/611,355

(22) PCT Filed: Mar. 25, 2021

(86) PCT No.: PCT/JP2021/012466
§ 371 (c)(1),
(2) Date: Nov. 15, 2021

(87) PCT Pub. No.: WO2021/215185
PCT Pub. Date: Oct. 28, 2021

(65) Prior Publication Data
US 2022/0218266 A1 Jul. 14, 2022

(30) Foreign Application Priority Data
Apr. 24, 2020 (JP) .................................. 2020-077811

(51) Int. Cl.
*G16H 20/30* (2018.01)
*A61B 5/00* (2006.01)
(Continued)

(52) U.S. Cl.
CPC .......... *A61B 5/4064* (2013.01); *A61B 5/7445* (2013.01); *G02B 27/017* (2013.01);
(Continued)

(58) Field of Classification Search
None
See application file for complete search history.

(56) References Cited

U.S. PATENT DOCUMENTS

2005/0216243 A1* 9/2005 Graham ................. G16H 40/67
703/11
2012/0108909 A1* 5/2012 Slobounov ............... A61B 5/16
600/300

FOREIGN PATENT DOCUMENTS

JP 2015228957 A 12/2015
JP 2019076290 A 5/2019
(Continued)

OTHER PUBLICATIONS

Japanese Office Action with an English translation dated Dec. 28, 2020 for Application No. JP 2020-077811.
(Continued)

*Primary Examiner* — Ankit D Tejani
(74) *Attorney, Agent, or Firm* — DiPerna Law Firm, P.C.

(57) ABSTRACT

To control a cognitive load to be given to the cognitive function of a user in rehabilitation, this invention provides a rehabilitation support apparatus including a detector that detects a three-dimensional rehabilitation action of the user, a display controller that generates, in a three-dimensional virtual space, an avatar object that moves in accordance with the detected rehabilitation action and a target object to be visually recognized by the user and displays these on a display, a notifier that notifies generation of the target object, and a cognitive load controller that gives a cognitive load to the user by generating the target object after an elapse of a predetermined time from the notification of the generation position of the target object.

8 Claims, 6 Drawing Sheets

(51) Int. Cl.
   *G02B 27/01*       (2006.01)
   *G06T 19/00*       (2011.01)
   *A63B 22/00*       (2006.01)
(52) U.S. Cl.
   CPC ........... *G06T 19/006* (2013.01); *G16H 20/30* (2018.01); *A63B 2022/0094* (2013.01); *G06T 2210/41* (2013.01)

(56) References Cited

FOREIGN PATENT DOCUMENTS

| | | | |
|---|---|---|---|
| JP | 2019076302 | A | 5/2019 |
| JP | 6531338 | B1 | 6/2019 |

OTHER PUBLICATIONS

International Search Report with an English translation dated May 11, 2021 for Application No. PCT/JP2021/012466.
English Abstract of JP 6531338.
English Abstract of JP 2019076302.
English Abstract of JP 2019076290.
English Abstract of JP 2015228957.

* cited by examiner

REHABILITATION SUPPORT APPARATUS, METHOD THEREFOR, AND PROGRAM

RELATED APPLICATION

This application is an application under 35 U.S.C. 371 of International Application No. PCT/JP2021/012466 filed on Mar. 25, 2021, the entire contents of which are incorporated herein by reference.

This application is based upon and claims the benefit of priority from Japanese patent application No. 2020-77811, filed on Apr. 24, 2020, the disclosure of which is incorporated herein in its entirety by reference.

TECHNICAL FIELD

The present invention relates to a rehabilitation support apparatus, a method therefor, and a program.

BACKGROUND ART

In the above technical field, patent literature 1 discloses a system configured to support rehabilitation.

CITATION LIST

Patent Literature

Patent literature 1: Japanese Patent Laid-Open No. 2015-228957

SUMMARY OF THE INVENTION

Technical Problem

However, in the technique described in the above literature, it is impossible to control a load to be given to the cognitive function of a user in rehabilitation.

The present invention enables to provide a technique of solving the above-described problem.

Solution to Problem

One example aspect of the invention provides a rehabilitation support apparatus for recovering one of cognitive impairment and a higher brain dysfunction, comprising:

a detector that detects a three-dimensional rehabilitation action of a user;

a display controller that generates, in a three-dimensional virtual space, an avatar object that moves in accordance with the detected rehabilitation action and a target object to be visually recognized by the user and displays the avatar object and the target object on a display;

a notifier that notifies a generation position of the target object; and a cognitive load controller that gives a cognitive load to the user by generating the target object after an elapse of a predetermined time from the notification of the generation position of the target object, wherein to control the cognitive load to be given to the user, the cognitive load controller changes the predetermined time by an operation of an operator.

Another example aspect of the invention provides a rehabilitation support apparatus for recovering one of cognitive impairment and a higher brain dysfunction, comprising:

a detector that detects a three-dimensional rehabilitation action of a user;

a display controller that generates, in a three-dimensional virtual space, an avatar object that moves in accordance with the detected rehabilitation action and a target object to be visually recognized by the user and displays the avatar object and the target object on a display;

a notifier that notifies a generation position of the target object; and a cognitive load controller that gives a cognitive load to the user by generating the target object after an elapse of a predetermined time from the notification of the generation position of the target object, wherein to control the cognitive load to be given to the user, the cognitive load controller causes at least two target objects to simultaneously exist in the three-dimensional virtual space.

Still other example aspect of the invention provides a rehabilitation support apparatus for recovering one of cognitive impairment and a higher brain dysfunction, comprising:

a detector that detects a three-dimensional rehabilitation action of a user;

a display controller that generates, in a three-dimensional virtual space, an avatar object that moves in accordance with the detected rehabilitation action and a target object to be visually recognized by the user and displays the avatar object and the target object on a display;

a notifier that notifies a generation position of the target object; and a cognitive load controller that gives a cognitive load to the user by generating the target object after an elapse of a predetermined time from the notification of the generation position of the target object, wherein to control the cognitive load to be given to the user, the cognitive load controller changes a background image other than the target object to be displayed on the display.

One example aspect of the invention provides a rehabilitation support method for recovering one of cognitive impairment and a higher brain dysfunction, comprising:

detecting a three-dimensional rehabilitation action of a user;

generating, in a three-dimensional virtual space, an avatar object that moves in accordance with the detected rehabilitation action and a target object to be visually recognized by the user and displaying the avatar object and the target object on a display;

notifying a generation position of the target object; and giving a cognitive load to the user by generating the target object after an elapse of a predetermined time from the notification of the generation position of the target object, wherein in the giving, to control the cognitive load to be given to the user, the predetermined time is changed by an operation of an operator.

Another example aspect of the invention provides a rehabilitation support method for recovering one of cognitive impairment and a higher brain dysfunction, comprising:

detecting a three-dimensional rehabilitation action of a user;

generating, in a three-dimensional virtual space, an avatar object that moves in accordance with the detected rehabilitation action and a target object to be visually recognized by the user and displaying the avatar object and the target object on a display;

notifying a generation position of the target object; and giving a cognitive load to the user by generating the target object after an elapse of a predetermined time from the notification of the generation position of the target object, wherein in the giving, to control the cognitive load to be given to the user, at least two target objects are caused to simultaneously exist in the three-dimensional virtual space.

Still other example aspect of the invention provides a rehabilitation support method for recovering one of cognitive impairment and a higher brain dysfunction, comprising:

detecting a three-dimensional rehabilitation action of a user;

generating, in a three-dimensional virtual space, an avatar object that moves in accordance with the detected rehabilitation action and a target object to be visually recognized by the user and displaying the avatar object and the target object on a display;

notifying a generation position of the target object; and giving a cognitive load to the user by generating the target object after an elapse of a predetermined time from the notification of the generation position of the target object, wherein in the giving, to control the cognitive load to be given to the user, a background image other than the target object to be displayed on the display is changed.

One example aspect of the invention provides a rehabilitation support program for recovering one of cognitive impairment and a higher brain dysfunction, the program causing a computer to execute a method, comprising:

detecting a three-dimensional rehabilitation action of a user;

generating, in a three-dimensional virtual space, an avatar object that moves in accordance with the detected rehabilitation action and a target object to be visually recognized by the user and displaying the avatar object and the target object on a display;

notifying a generation position of the target object; and giving a cognitive load to the user by generating the target object after an elapse of a predetermined time from the notification of the generation position of the target object, wherein in the giving, to control the cognitive load to be given to the user, the predetermined time is changed by an operation of an operator.

Another example aspect of the invention provides a rehabilitation support program for recovering one of cognitive impairment and a higher brain dysfunction, the program causing a computer to execute a method, comprising:

detecting a three-dimensional rehabilitation action of a user;

generating, in a three-dimensional virtual space, an avatar object that moves in accordance with the detected rehabilitation action and a target object to be visually recognized by the user and displaying the avatar object and the target object on a display;

notifying a generation position of the target object; and giving a cognitive load to the user by generating the target object after an elapse of a predetermined time from the notification of the generation position of the target object, wherein in the giving, to control the cognitive load to be given to the user, at least two target objects are caused to simultaneously exist in the three-dimensional virtual space.

Still other example aspect of the invention provides a rehabilitation support program for recovering one of cognitive impairment and a higher brain dysfunction, the program causing a computer to execute a method, comprising:

detecting a three-dimensional rehabilitation action of a user;

generating, in a three-dimensional virtual space, an avatar object that moves in accordance with the detected rehabilitation action and a target object to be visually recognized by the user and displaying the avatar object and the target object on a display;

notifying a generation position of the target object; and giving a cognitive load to the user by generating the target object after an elapse of a predetermined time from the notification of the generation position of the target object, wherein in the giving, to control the cognitive load to be given to the user, a background image other than the target object to be displayed on the display is changed.

Advantageous Effects of Invention

According to the present invention, it is possible to control a load to be given to the cognitive function of a user in rehabilitation.

DESCRIPTION OF EXAMPLE EMBODIMENTS

Example embodiments of the present invention will now be described in detail with reference to the drawings. It should be noted that the relative arrangement of the components, the numerical expressions and numerical values set forth in these example embodiments do not limit the scope of the present invention unless it is specifically stated otherwise.

First Example Embodiment

Figure 1:
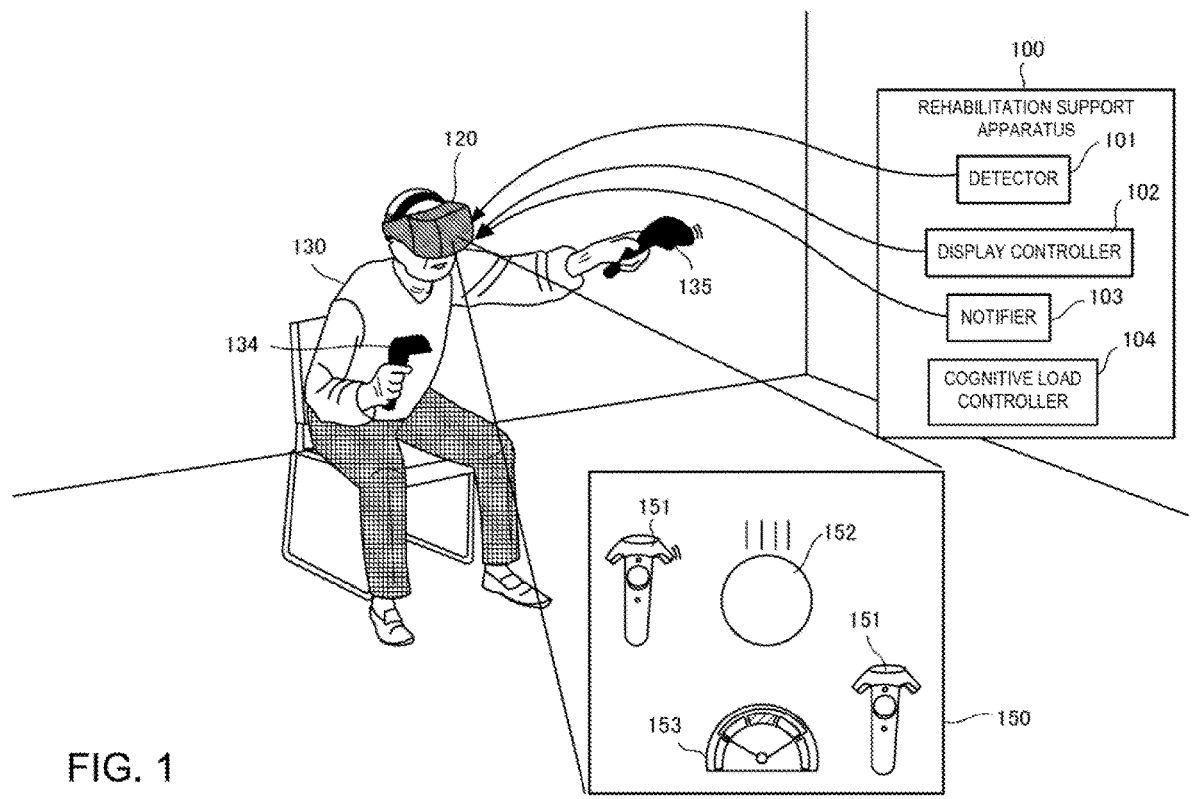
FIG. 1 is a block diagram showing the configuration of a rehabilitation support apparatus according to the first example embodiment.

A rehabilitation support apparatus 100 according to the first example embodiment of the present invention will be described with reference to FIG. 1.

The rehabilitation support apparatus 100 includes a detector 101, a display controller 102, a notifier 103, and a cognitive load controller 104.

The detector 101 detects the direction of the head of a user 130 who wears a head mounted display 120, and a three-dimensional rehabilitation action.

The display controller 102 generates, in a three-dimensional virtual space 150, avatar objects 151 that move in accordance with a detected rehabilitation action and a target object 152 to be visually recognized by the user 130. The display controller 102 then displays the objects on the head mounted display 120 in accordance with the direction of the head of the user 130 detected by the detector 101.

The notifier 103 notifies the user of the generation of the target object 152. For example, in FIG. 1, the notifier 103 displays, as a notification image 153, a radar screen image used to notify the user of the generation position of the target object 152. The radar screen image indicates the direction in which the target object 152 is located relatively with respect to a reference direction (initially set in the front direction of the user who is sitting straight on a chair) in the virtual space. The radar screen image also indicates the direction in which the head of the user 130 is located relatively with respect to the reference direction.

The cognitive load controller 104 generates the target object 152 after the elapse of a predetermined time from the timing of notifying the generation of the target object 152, thereby giving a cognitive load to the user 130.

As described above, according to this example embodiment, the user needs to continuously memorize and hold a rehabilitation action that he/she should perform after notification of generation of the target object until actual generation of the target object. It is therefore possible to quantitatively adjust and control a cognitive load that should be subjected to information processing by the brain and then give it to the user. For example, when the type, number, size, spatial spread, position, amount, and the like of information included in a notification image or a notification sound are adjusted, a cognitive load that has increased the complexity of information to be memorized and held can be given.

Second Example Embodiment

Figure 2A:
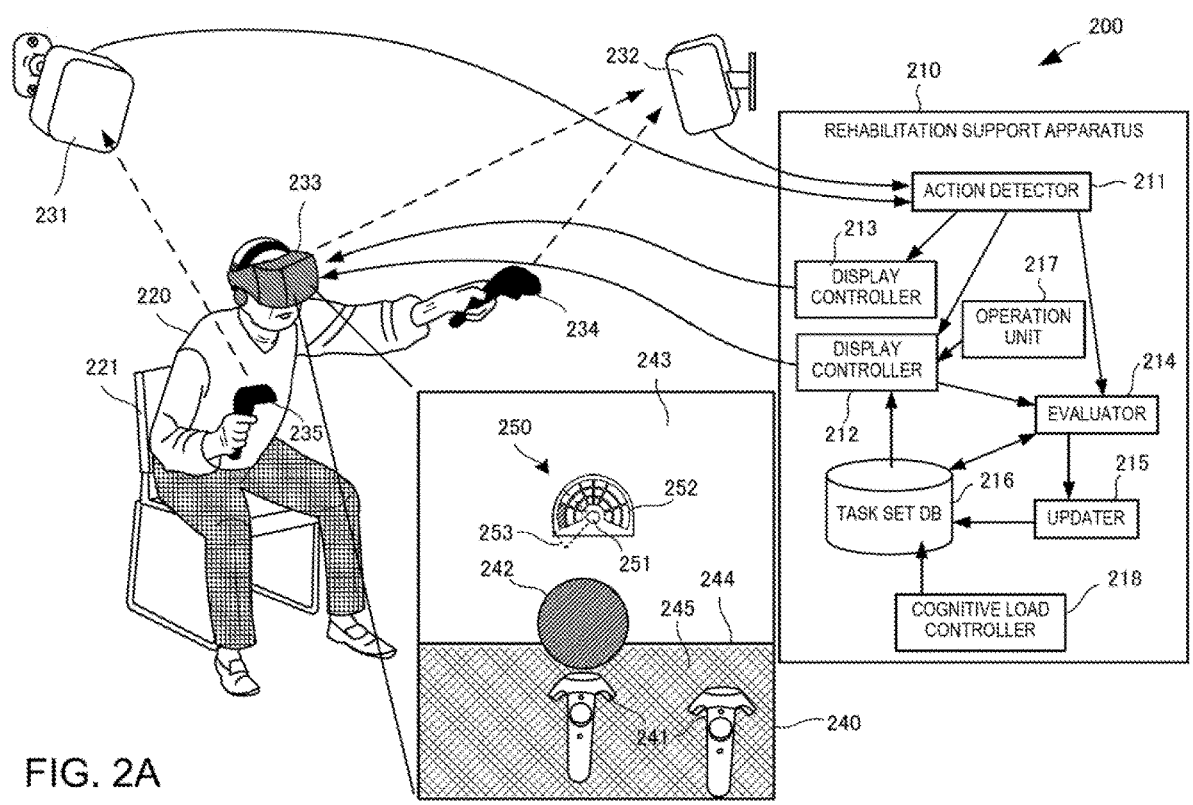
FIG. 2A is a block diagram showing the configuration of a rehabilitation support apparatus according to the second example embodiment.

A rehabilitation support system 200 according to the second example embodiment of the present invention will be described with reference to FIG. 2A. FIG. 2A is a view for explaining the configuration of the rehabilitation support system 200 according to this example embodiment.

As shown in FIG. 2A, the rehabilitation support system 200 includes a rehabilitation support apparatus 210, two base stations 231 and 232, a head mounted display 233, and two controllers 234 and 235. A user 220 sitting on a chair 221 twists the upper half body or stretches the hands in accordance with display on the head mounted display 233, thereby making a rehabilitation action. In this example embodiment, a description will be made assuming rehabilitation performed while sitting on a chair. However, the present invention is not limited to this. Rehabilitation may be performed while standing, walking, running, or making another specific action. In addition, the controllers may be held on or attached to body parts other than hands, such as feet or trunk.

The two base stations 231 and 232 sense the motion of the head mounted display 233 and the motions of the controllers 234 and 235, and send these to the rehabilitation support apparatus 210. The rehabilitation support apparatus 210 performs display control of the head mounted display 233 while evaluating the rehabilitation action of the user 220. Note that the head mounted display 233 can be of a non-transmissive type, a video see-through type, or optical see-through type. In this example embodiment, a virtual space of VR (Virtual Reality) is presented to the user. However, a physical space and a virtual space may be displayed in a superimposed manner, like AR (Augmented Reality), or physical information may be reflected on a virtual space, like MR (Mixed Reality).

In this example embodiment, as an example of a sensor configured to detect the position or action of the hand or head of the user, the controllers 234 and 235 held in the hands of the user 220, and the base stations 231 and 232 have been described. However, the present invention is not limited to this. A camera (including a depth sensor) configured to detect the positions or action of the hands of the user by image recognition processing, a sensor configured to detect the positions of the hands of the user by a temperature, a wristwatch-type wearable terminal put on an arm of the user, a motion capture device, or the like can be applied to the present invention.

The rehabilitation support apparatus 210 includes an action detector 211, display controllers 212 and 213, an evaluator 214, an updater 215, a task set database 216, and an operation unit 217.

The action detector 211 acquires, via the base stations 231 and 232, the positions of the controllers 234 and 235 held in the hands of the user 220, and detects the rehabilitation action of the user 220 based on changes in the positions of the hands of the user 220.

The display controller 212 generates, in a virtual space, avatar objects 241 that move in accordance with a detected rehabilitation action and a target object 242 representing the target of the rehabilitation action. The display controller 212 displays, on a display screen 240, the images of the avatar objects 241 and the target object 242 in accordance with the direction and position of the head mounted display 233 detected by the action detector 211. The images of the avatar objects 241 and the target object 242 are superimposed on a background image 243. Here, the avatar objects 241 have the same shape as the controllers 234 and 235. However, the present invention is not limited to this, and the size, shape, or color may be changed on the left and right sides. The avatar objects 241 move in the display screen 240 in accordance with the motions of the controllers 234 and 235. The controllers 234 and 235 are each provided with at least one button and configured to perform various kinds of settings by operating the button. The background image 243 is cut out from a virtual space including a horizontal line 244 and a ground surface image 245.

The display controller 212 displays the target object 242 while gradually changing its display position and size such that it falls downward from above the user 220. The user 220 moves the controllers 234 and 235 to make the avatar objects 241 in the screen close to the target object 242. Note that as for the moving direction of the target object, for example, the target object may be displayed such that it rises from the floor surface to above the head, or movement in the depth direction may occur in addition to the movement in the vertical direction.

If the shortest distance between the target object 242 and a sensor object (not shown here) included in the avatar object 241 falls within a predetermined range, the target is achieved, and the target object 242 disappears. At this time, if the shortest distance between the target object 242 and the sensor object included in the avatar object 241 is equal to or less than a first threshold, "excellent" is displayed because of the complete achievement of the target, and a corresponding voice is output to make feedback. The controllers 234 and 235 may simultaneously be vibrated.

On the other hand, if the shortest distance between the target object 242 and the sensor object included in the avatar object 241 is not less than the first threshold and not more than a second threshold, "well done" is displayed because of the achievement of the target, and a corresponding voice is output to make feedback. The controllers 234 and 235 may simultaneously be vibrated.

The action of the user 220 to move the controllers 234 and 235 is the rehabilitation action, and the display of the target object that urges the user 220 to do one rehabilitation action he/she should make is called a task. Information (task data) representing one task includes the appearance direction of the target object, the shape, the appearance position (the distanced from the user), the appearance interval (time interval), the moving speed in failing or rising, the size, the color, which one of the left and right controllers should be used to acquire a target object, the number of target objects that appear simultaneously, the size of the sensor object, and the like.

That is, the display controller 212 can also change (for example, in three levels), in accordance with task data, the distance from the user 220 to the fall position of the target object 242 in the depth direction. For example, a change can be made such that the target object falls quite near the user 220 or falls to a position that the user 220 cannot reach unless largely inclining the body forward. This can control an exercising load to be given to the user.

The display controller 213 displays a radar screen image 250 on the display screen 240 of the head mounted display 233. The radar screen image 250 is a notification image used to notify the user of generation of the target object 242. The radar screen image 250 notifies the user of the direction in which the generated target object 242 is located relatively with respect to a reference direction (initially set in the front direction of the user who is sitting straight on a chair) in the virtual space. The radar screen image 250 also notifies the user how far the position of the generated target object 242 is apart from the user 220. Note that the notification image is not limited to the radar screen image, and the notification may be made using characters, an arrow, a symbol, an illustration, or a type, intensity, blinking, or the like of light or a color. The notification method is not limited to the image, and may use a voice, a vibration, or a combination of some of a voice, a vibration, and an image.

Independently of the direction of the head of the user 220, the display controller 213 displays the radar screen image 250 at the center (for example, within the range of −50° to 50°) of the display screen 240 of the head mounted display 233. However, the display portion is not limited to the center, and may be, for example, an arbitrary place on the four corners, the upper end, the lower end, the left end, and the right end of the screen.

The radar screen image 250 includes a head image 251 representing the head of the user viewed from above, a block image 252 obtained by dividing the periphery of the head image 251 into a plurality of blocks, and a fan-shaped image 253 as a visual field image representing the visual field of the user. A target position image representing the position of a target object is shown by coloring, blinking, or lighting a block in the block image 252. This allows the user 220 to know whether the target object exists on the left side or the right side with respect to the direction in which he/she faces. Note that in this example embodiment, the block image 252 is fixed, and the fan-shaped image 253 moves. However, the present invention is not limited to this, and the block image 252 may be moved in accordance with the direction of the head while fixing the fan-shaped image 253 and the head image 251. More specifically, if the head turns to the left, the block image 252 may rotate to right.

The evaluator 214 evaluates the rehabilitation action of the user in accordance with the amount and quality of the task achieved by the user 220 and adds a point. Here, the quality of the achieved task depends on "well done" or "excellent", that is, how close the avatar object could be brought to the target object. The evaluator 214 adds different points to achieved tasks (a high point to a far object, and a low point to a close object).

The updater 215 updates a target task in accordance with the integrated point. For example, a target task may be updated using a task achievement ratio (the number of achieved targets/the number of tasks).

The task set database 216 stores a set of a plurality of tasks. The task set database 216 stores a task set that decides the order of providing the plurality of tasks to the user.

For example, task sets may be stored as templates for each hospital, or a history of executed task sets may be stored for each user. The rehabilitation support apparatus 210 may be configured to be communicable with another rehabilitation support apparatus via the Internet. In this case, one task set may be executed by the same user in a plurality of places, or various templates may be shared by a plurality of users in remote sites.

The operation unit 217 is provided to operate display control in the display controller 212 and the display controller 213.

A cognitive load controller 218 generates the target object 242 after the elapse of a predetermined time from the timing of notifying the generation of the target object 242, thereby giving a cognitive load to the user 220. That is, the user needs to continuously memorize and hold an action that he/she should perform after he/she knows that the target object will be generated until actual generation of the target object. The "request to memorize" is a cognitive load for the user. The cognitive load controller 218 may control the cognitive load by changing a predetermined time from the timing of notifying the generation of the target object 242 to the timing of generating the target object 242.

Also, the cognitive load controller 218 may control the cognitive load by changing the time not "until the timing of generating the target object 242" but "until the target object 242 approaches the range the user 220 can reach".

The cognitive load controller 218 may give a cognitive load to the user 220 by displaying the background image 243 other than the target object 242 on the head mounted display 233.

Figure 2B:
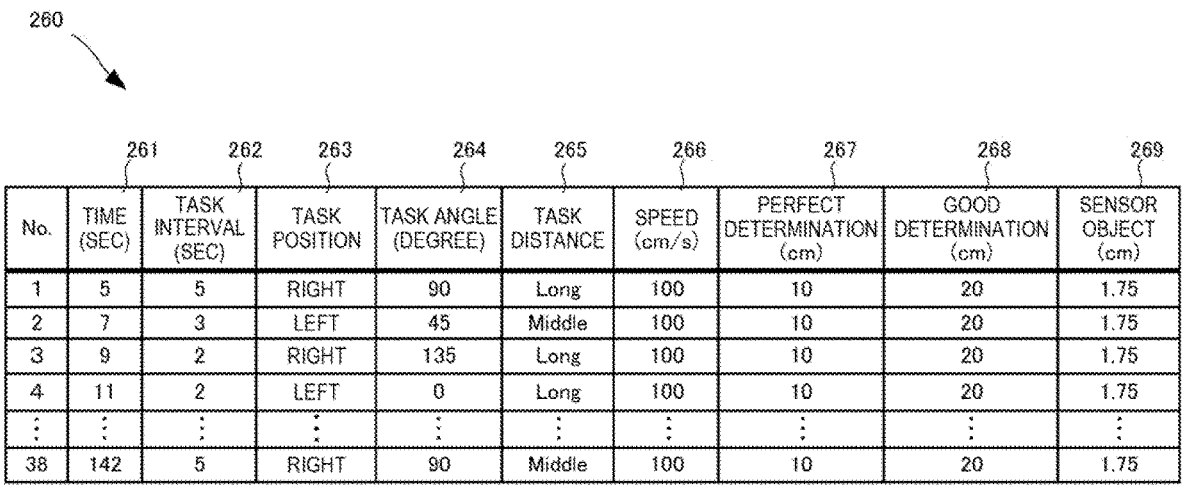
FIG. 2B is a view showing the task database configuration of the rehabilitation support apparatus according to the second example embodiment.

FIG. 2B is a view showing a task table 260 stored in the task set database 216. In the task table 260, a time (task generation timing) 261, a task interval 262, a task position 263, a task angle 264, and a task distance (intensity) 265 are stored in linkage with a task ID. Also, in the task table 260, a target object speed 266, a perfect determination "excellent evaluation" criterion 267, a good determination (well done evaluation) criterion 26g8, a sensor object size 269, and the like are stored in linkage with a task ID. In addition to these, a delay time (predetermined time) from task generation notification to task generation may be set for each task.

Figure 3:
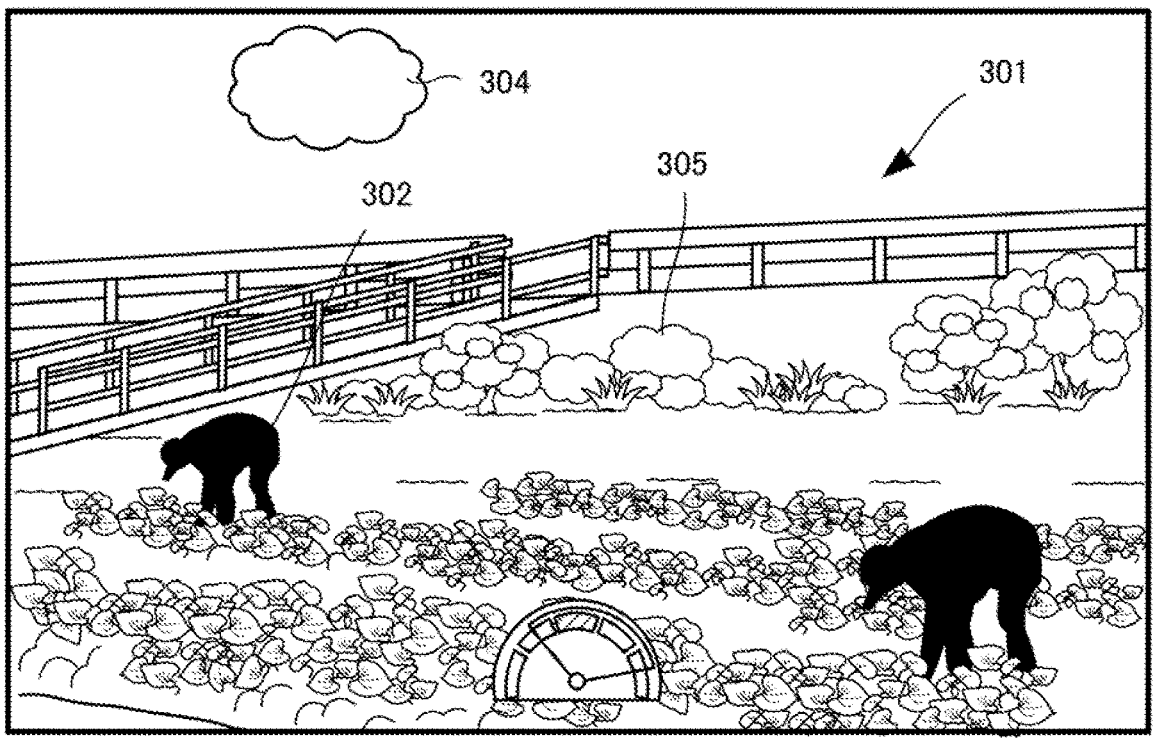
FIG. 3 is a view showing an example of the display screen of the rehabilitation support apparatus according to the second example embodiment.
Figure 3:
Figure 3:
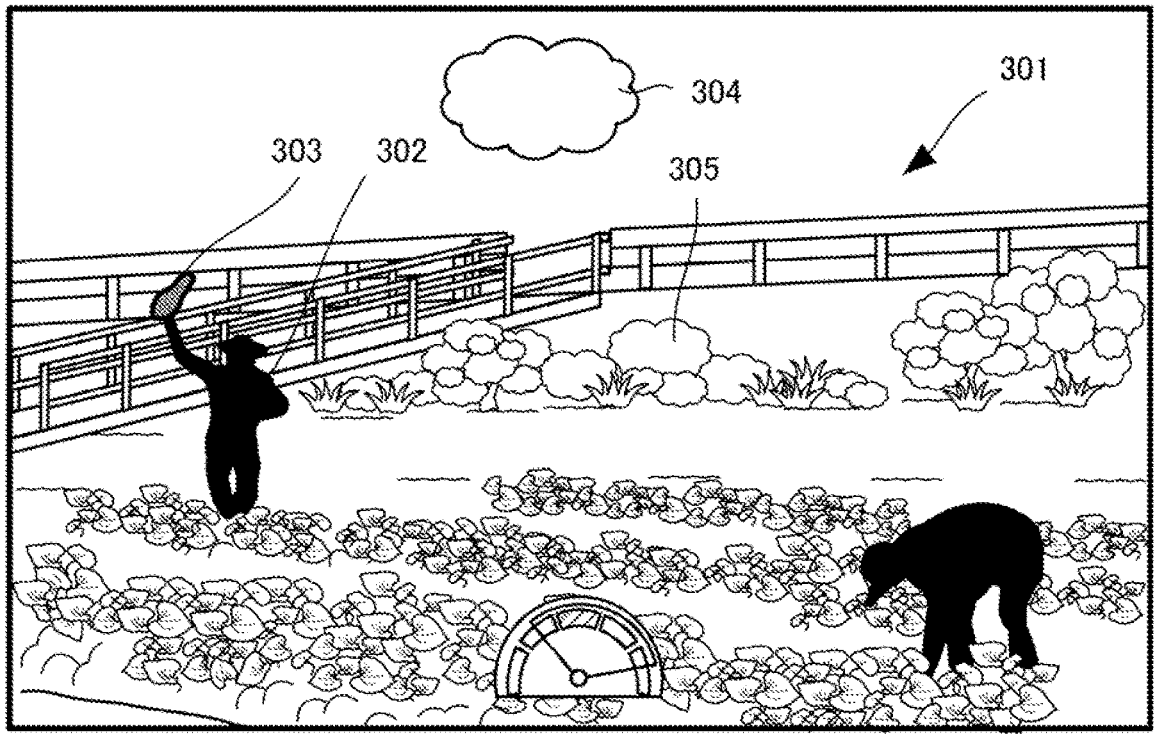
Figure 4:
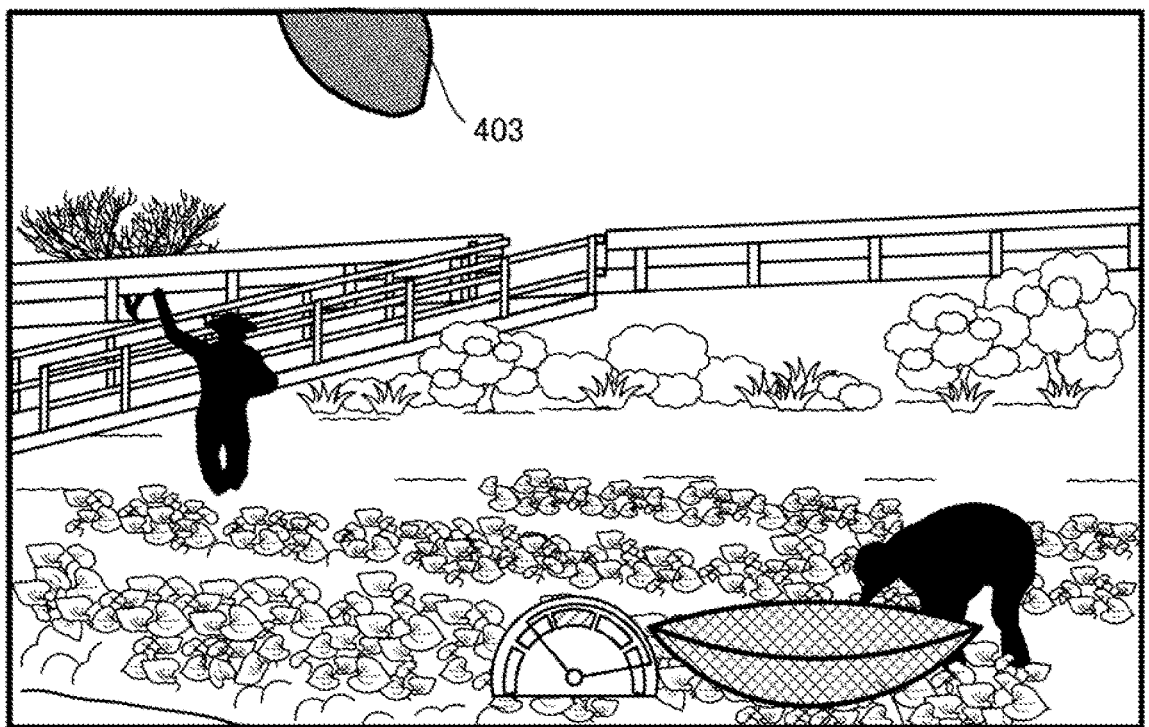
FIG. 4 is a view showing an example of the display screen of the rehabilitation support apparatus according to the second example embodiment.
Figure 4:
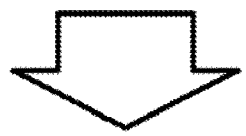
Figure 4:
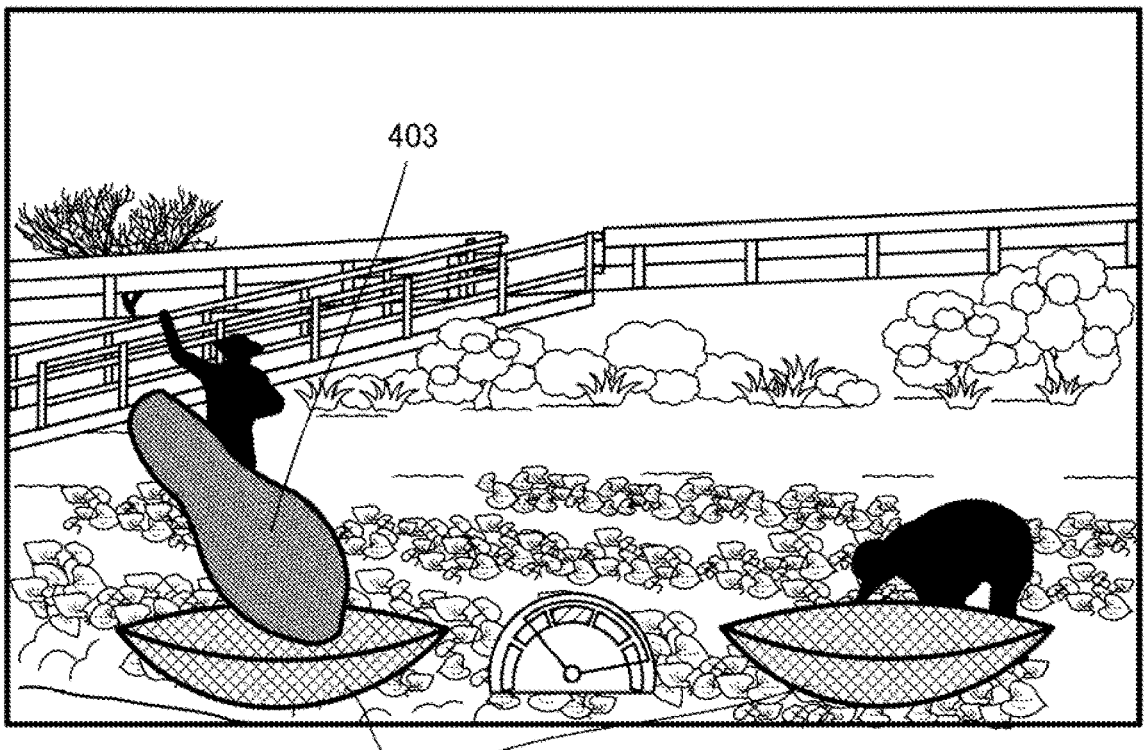
Figure 5:
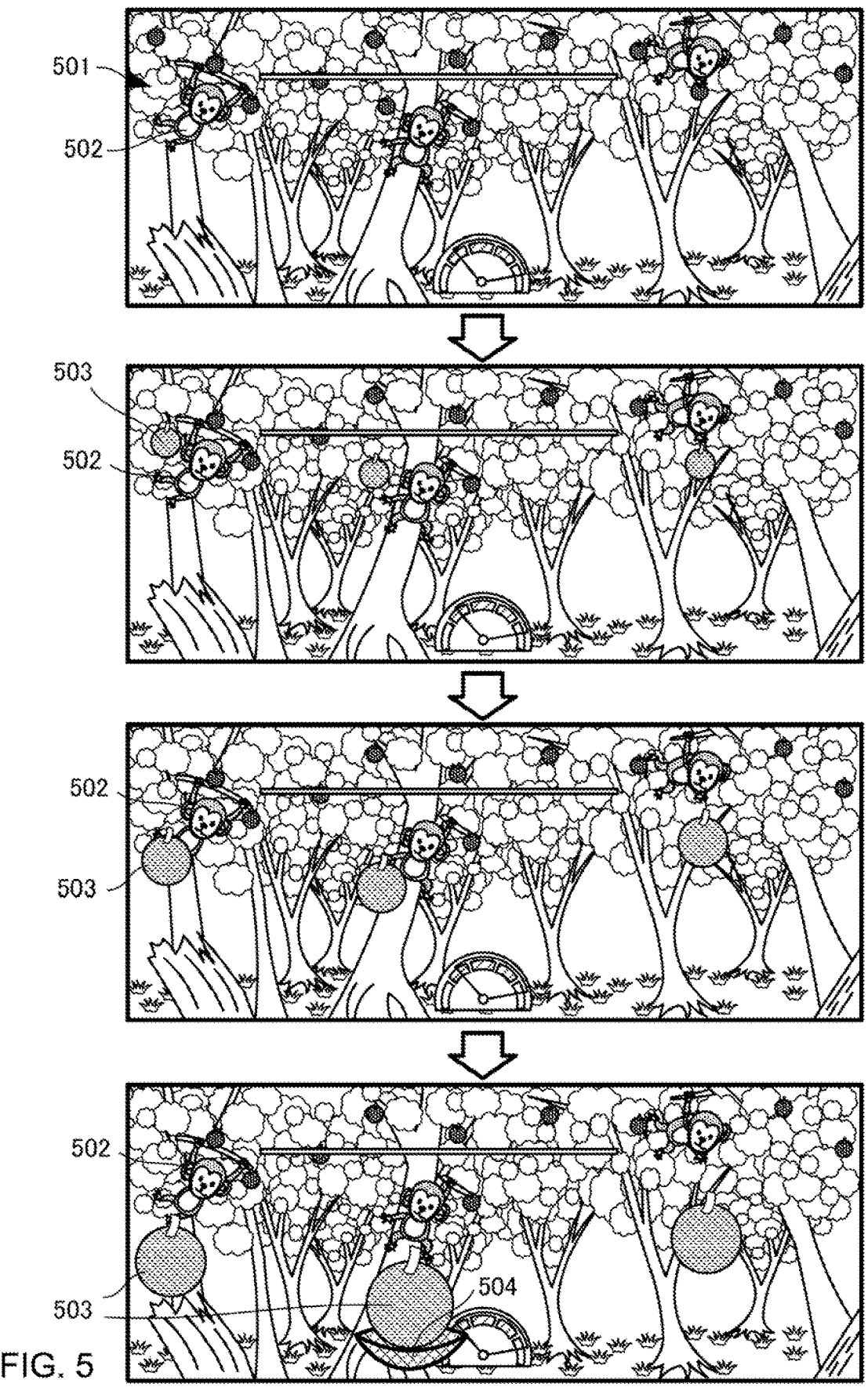
FIG. 5 is a view showing an example of the display screen of the rehabilitation support apparatus according to the second example embodiment.

FIGS. 3 to 5 are views showing examples of display on the display screen 240 according to this example embodiment. In FIGS. 3 and 4, on a background image 301 representing a field, an image of a person representing a farmer is displayed as a trigger object 302 serving as a trigger of target object appearance. That is, the display controller 213 displays the trigger object 302 as a notification image used to notify the user of generation of the target object 242.

When a predetermined time elapses after the trigger object 302 throws up a target object 303 in the shape of a potato, a target object 403 having the shape of a large potato appears from the upper side of the screen, as shown in FIG. 4. When the falling target object 403 is received by moving an avatar object 402 having the shape of a basket, the task is achieved. The left and right avatar objects 402 move on the screen in synchronism with the motions of the controllers 234 and 235.

The cognitive load controller 218 generates the target object 403 after the elapse of a predetermined time from the timing at which the trigger object 302 throws up the target object 303 and notifies the generation of the target object 303, thereby giving a cognitive load to the user 220. Note that in synchronism with the motion of the trigger object 302, generation of the target object may be notified at the same timing using a radar chart type notification image, or a notification by a voice may be combined.

In this way, the cognitive load controller 218 displays not a background including only a horizontal line as shown in FIG. 2A but a background image including a large quantity of information as shown in FIGS. 3 and 4, thereby giving a cognitive load to the user. That is, it is made difficult to memorize that the target object 401 has appeared, and the position to which the target object 401 is expected to fall, thereby giving a load closer to a cognitive load necessary in a real life to the user of rehabilitation.

In particular, the cognitive load controller 218 changes at least a part of the background image 301 along with time, thereby giving a cognitive load to the user 220. In the example shown in FIG. 3, for example, in the background image 301, a cloud 304 may be moved, plants 305 may be shaken, or an animal (not shown) irrelevant to the target object may be made to appear. This can impede concentration to the target object 303 and make it more difficult for the user 220 to memorize the position to which the target object 303 is expected to fall. More technically, it can be said that information irrelevant to the task is displayed on the background image to prepare an environment in which it is difficult to concentrate to the target object and intentionally cause an attention disorder (more specifically, a selective attention disorder, a divided attention disorder, an alternating attention disorder, or a sustained attention disorder), thereby making memorization difficult and controlling the cognitive load.

FIG. 5 is a view showing another example of display on the display screen 240 according to this example embodiment. In FIG. 5, in a background image 501 like woods, a trigger object 502 representing a monkey and a target object 503 representing an apple are displayed. When the trigger object 502 representing a monkey drops the target object 503 representing an apple from a tree, and the target object 503 approaching the user is received by moving an avatar object 504 representing a basket, the task is achieved. In this case as well, the cognitive load controller 218 starts dropping the target object 503 after the elapse of a predetermined time from the timing at which the trigger object 502 shakes the tree and notifies the generation of the target object 503, thereby giving a cognitive load to the user 220 while causing an attention disorder.

Also, the cognitive load controller 218 causes at least two target objects 503 to exist in the three-dimensional virtual space and display these on the display screen 240, thereby giving a cognitively stronger load to the user 220. In other words, the cognitive load controller 218 generates the at least two target objects 503 at different positions in the left-and-right direction in the three-dimensional virtual space. That is, since the user 220 needs to memorize a plurality of points concerning at which position the trigger object 502 shakes the tree, a cognitively stronger load is given.

In particular, since the at least two target objects 503 are generated at a plurality of positions in a direction (the left-and-right direction in FIG. 5) different from the moving direction (the falling direction in FIG. 5) of the target object 503, a larger cognitive load can be given. That is, since the user 220 needs to move the controllers 234 and 235 in consideration of the movement in the vertical direction, the difference between the generation positions in the left-and-right direction, and the difference in the failing position in the depth direction, the spatial cognitive ability is also tested. As described above, when the type, number, size, spatial spread, position, amount, and the like of information included in a notification image including a trigger object or a notification sound are adjusted in addition to the change of the predetermined time of the task, it is possible to quantitatively adjust and control the complexity of information to be memorized and held, that is, a cognitive load that should be subjected to information processing by the brain of the user.

The evaluator 214 evaluates the cognitive ability of the user based on whether the avatar object has reached, in a good timing, a three-dimensional target position represented by the target object, the time interval from target object generation notification to generation and the number of target objects, the degree of the attention disorder caused by the background image, and the like.

As described above, according to this example, it is possible to effectively control the load to be given to the cognitive function of the user in rehabilitation. More specifically, the memory and the cognitive processing ability of the user are tested quite naturally in a very easy task to receive a ball, a potato, or an apple, instead of memorizing something in accordance with an instruction for memorizing. For this reason, the psychological burden is small, and a rejection or an adverse reaction to rehabilitation, or a depressive reaction in case of a failure hardly occurs. By the rehabilitation action according to this example embodiment, it is possible to recover a so-called cognitive ability and a higher brain function (disorder) including a memory, a cognitive processing ability, a spatial cognitive ability, and an attention function (disorder) together with an exercise capacity and make a guidance such that the user can live his/her everyday life comfortably.

Note that in the example embodiment, a head mounted display is used. However, an eyeglass type display suffices. In place of the head mounted display, a hologram or a large TV type display may be arranged on the periphery of the user to urge the user to make a rehabilitation action.

OTHER EXAMPLE EMBODIMENTS

While the invention has been particularly shown and described with reference to example embodiments thereof, the invention is not limited to these example embodiments. It will be understood by those of ordinary skill in the art that various changes in form and details may be made therein without departing from the spirit and scope of the present invention as defined by the claims. A system or apparatus including any combination of the individual features included in the respective example embodiments may be incorporated in the scope of the present invention.

The present invention is applicable to a system including a plurality of devices or a single apparatus. The present invention is also applicable even when an information processing program for implementing the functions of example embodiments is supplied to the system or apparatus directly or from a remote site. Hence, the present invention also incorporates the program installed in a computer to implement the functions of the present invention by the computer, a medium storing the program, and a WWW (World Wide Web) server that causes a user to download the program. Especially, the present invention incorporates at least a non-transitory computer readable medium storing a program that causes a computer to execute processing steps included in the above-described example embodiments.

The invention claimed is:

1. A rehabilitation support apparatus for recovering one of cognitive impairment and a higher brain dysfunction of a user, comprising:
   a detector that detects a three-dimensional rehabilitation action of the user;
   a display controller that generates, in a three-dimensional virtual space, an avatar object that moves in accordance with the detected rehabilitation action and a target object to be visually recognized by the user and displays the avatar object and the target object on a display, wherein the rehabilitation action of the user is capable of moving the avatar object relative to the target object so as to enable the user to bring the avatar object and target object into proximity with one another;
   a notifier that notifies a generation position, in the three-dimensional virtual space, of the target object;
   a cognitive load controller that gives a cognitive load to the user by generating the target object after a lapse of a predetermined time from the notification of the generation position of the target object, and
   a task table that sets a task requiring the user to move the avatar object into proximity with the target object, wherein success in performance of the task is facilitated if, after the lapse of time, the user remembers the generation position of the target object notified by the notifier;
   wherein to control the cognitive load to be given to the user, said cognitive load controller is configured to change the predetermined time by an operation of an operator such that an increase in the predetermined time increases a complexity of the task.

2. The rehabilitation support apparatus according to claim 1, further comprising an evaluator that evaluates a cognitive ability of the user based on whether the avatar object has reached, in a good timing, a three-dimensional target position represented by the target object by the rehabilitation action, and the predetermined time.

3. A rehabilitation support apparatus for recovering one of cognitive impairment and a higher brain dysfunction of a user, comprising:
   a detector that detects a three-dimensional rehabilitation action of the user;
   a display controller that generates, in a three-dimensional virtual space, an avatar object that moves in accordance with the detected rehabilitation action and at least two target objects to be visually recognized by the user and displays the avatar object and the at least two target objects on a display, wherein the rehabilitation action of the user is capable of moving the avatar object relative to the target objects so as to enable the user to bring the avatar object into proximity with the target objects;
   a notifier that notifies a generation position, in the three-dimensional virtual space, of the at least two target objects;
   a cognitive load controller that gives a cognitive load to the user by generating the at least two target objects after a lapse of a predetermined time from the notification of the generation position of the at least two target objects, and
   a task table that sets a task requiring the user to move the avatar object into proximity with a first of the at least two target objects, wherein success in performance of the task is facilitated if, after the lapse of time, the user remembers the generation position of the first target object notified by the notifier;
   wherein to control the cognitive load to be given to the user, said cognitive load controller causes the at least two target objects to simultaneously exist in the three-dimensional virtual space at different positions in the display.

4. The rehabilitation support apparatus according to claim 3, wherein
   said display controller moves the at least two target objects in a vertical direction in the three-dimensional virtual space, and
   said cognitive load controller generates the at least two target objects at different positions in a left-and-right direction in the three-dimensional virtual space, thereby giving the cognitive load to the user.

5. The rehabilitation support apparatus according to claim 4, further comprising an evaluator that evaluates a cognitive ability of the user based on whether the avatar object has reached, in a good timing, a three-dimensional target position represented by the first target object by the rehabilitation action, and the predetermined time.

6. The rehabilitation support apparatus according to claim 3, further comprising an evaluator that evaluates a cognitive ability of the user based on whether the avatar object has reached, in a good timing, a three-dimensional target position represented by the first target object by the rehabilitation action, and the predetermined time.

7. A rehabilitation support apparatus for recovering one of cognitive impairment and a higher brain dysfunction of a user, comprising:
   a detector that detects a three-dimensional rehabilitation action of the user;
   a display controller that generates, in a three-dimensional virtual space, an avatar object that moves in accordance with the detected rehabilitation action and a target object to be visually recognized by the user and displays the avatar object and the target object on a display, wherein the rehabilitation action of the user is capable of moving the avatar object relative to the target object so as to enable the user to bring the avatar object into proximity with the target object;
   a notifier that notifies a generation position, in the three-dimensional virtual space, of the target object;
   a cognitive load controller that gives a cognitive load to the user by generating the target object after a lapse of a predetermined time from the notification of the generation position of the target object, and
   a task table that sets a task requiring the user to move the avatar object into proximity with the target object, wherein success in performance of the task is facilitated if, after the lapse of time, the user remembers the generation position of the target object notified by the notifier;
   wherein to control the cognitive load to be given to the user, said cognitive load controller changes at least a part of a background image other than the target object to be displayed on the display along with time.

8. The rehabilitation support apparatus according to claim 7, further comprising an evaluator that evaluates a cognitive ability of the user based on whether the avatar object has reached, in a good timing, a three-dimensional target position represented by the target object by the rehabilitation action, and the predetermined time.

* * * * *